US009832966B2

(12) United States Patent
Narasimhamoorthy et al.

(10) Patent No.: US 9,832,966 B2
(45) Date of Patent: Dec. 5, 2017

(54) OREGANO CLONAL LINE HAVING HIGH LEVELS OF CARVACROL

(71) Applicant: Kemin Industries, Inc., Des Moines, IA (US)

(72) Inventors: Brindha Narasimhamoorthy, West De Moines, IA (US); John A. Greaves, Ankeny, IA (US); Liuqing Zhao, Zhuhai (CN); Zhiqiang Qui, Qinzhou (CN); Norman Cloud, Ames, IA (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 0 days.

(21) Appl. No.: 14/271,604

(22) Filed: May 7, 2014

(65) Prior Publication Data

US 2014/0336421 A1 Nov. 13, 2014

Related U.S. Application Data

(60) Provisional application No. 61/855,067, filed on May 7, 2013.

(51) Int. Cl.
*A01H 5/12* (2006.01)
*C07C 39/06* (2006.01)

(52) U.S. Cl.
CPC .............. *A01H 5/12* (2013.01); *C07C 39/06* (2013.01)

(58) Field of Classification Search
None
See application file for complete search history.

(56) References Cited

U.S. PATENT DOCUMENTS

| | | |
|---|---|---|
| 2001/0003654 A1 | 6/2001 | Shetty |
| 2004/0234968 A1 | 11/2004 | Croteau et al. |

FOREIGN PATENT DOCUMENTS

| | | |
|---|---|---|
| CA | 2281282 | 9/2000 |
| WO | 9828435 | 7/1998 |

OTHER PUBLICATIONS

Kirimer et al 1995, Chemistry of Natural Compounds 31(1): 37-41.*
Grime et al 1988, Comparative Plant Ecology; A functional approach to common British species, Springer, p. 422.*
Arafeh et al 2006, Jordan Journal of Agricultural Science 2(3): 274-282.*
Allan, Peter et al., "Oregano Improves Reproductive Performance of Sows", Jun. 2003, pp. 716-721, vol. 63.
Azizi et al., "Herbage Yield, essential oil content and composition of three oregano (*Origanum vulager* L.) populations as affected by soil moisture regimes and nitrogen supply", "Industrial Crops and Products", 2009, pp. 554-561, vol. 29.
Azizi et al., "Intraspecific diversity and relationship between subspecies of *Origanum vulgare* revealed by comparative AFLP and SAMPL marker analysis", "Plant Syst Evol", 2010.
Bendahou et al., "Antimicrobial activity and chemical composition of *Origanum glandulosum* Desf. essential oil and extract obtained by microwave extraction: Comparison with hydrodistillation", "Food Chemistry", 2008, pp. 132-139, vol. 106.
De Mastro et al., "Agronomic and Technological Assesment of Oregano (*Origanum vulagare* ssp.) Biotypes", "Acta Horticulturae", 2004, pp. 355-364, vol. 629.
Dunford, N.T. et al., "Effect of water stress on plant growth and thymol and carvacrol concentrations in Mexican oregano grown under controlled conditions", "Journal of Applied Horticulture", 2005, pp. 20-22, vol. 7.
Manzanilla et al., "Effect of plant extracts and formic acid on the intestinal equilibrium of early-weaned pigs", "Journal of Animal Science", 2005, pp. 3210-3218, No. 82.
Putievsky et al., "Cultivation, selection and conservation of Oregano species in Israel conditions", "Proceedings of the IPGRI International Workshop on Oregano", 2005, Published in: Italy.
Sangwan et al., "Regulation of essential oil production in plants", "Plant Growth Regulation", 2001, pp. 3-21, vol. 34.
Toncer et al., "Changes in essential oil composition of oregano (*O. onites* L.) due to diurnal variations at different developmental stages", "Notulae Botanicae Horti Agrobotanici", 2009, pp. 177-181, vol. 37.
Yaldiz et al., "Seasonal and diurnal variability of essential oil and its components in *Origanum onites* L. grown in the ecological conditions of Cukurova", "Grasas. Y. Aceites", 2005, pp. 254-258, vol. 56.
Kirimer et al, "Carvacrol-Rich Plants in Turkey", "Chemistry of Natural Compounds", Jan. 1, 1995, pp. 37-41, vol. 31, No. 1.
Economou et al, "Variability in essential oil content and composition of Origanum hirtum L., Origanum onites L., Coridothymus capitatus (L.) and Satureja thymbta L. populations from The Greek iland Lkaria", Industrial Crops and Products, Jan. 1, 2011, pp. 236-241, vol. 33, No. 1.
Figiel et al., "Composition of oregano essential oil (Origanum vulgate) as affected by drying method", "Journal of Food Engineering", May 1, 2010, vol. 98, No. 2, Published in: GB.
Goliaris et al., "Production of Greek Oregano Clones and Analysis of Their Essential Oils", "Journal of Herbs, Spices and Medicinal Plants", Jan. 6, 2003, pp. 29-35, vol. 10, No. 1.
European Patent Office, "Extended: European Search Report," issued in connection with European Patent Application No. 14795431.7. dated Nov. 30, 2016, 6 pages.

* cited by examiner

*Primary Examiner* — David H Kruse
(74) *Attorney, Agent, or Firm* — Nyemaster Goode P.C.

(57) ABSTRACT

A new and distinct clonal line of oregano named KI-Ov1750 and characterized by elevated levels of carvacrol and vigorous growth.

11 Claims, 5 Drawing Sheets

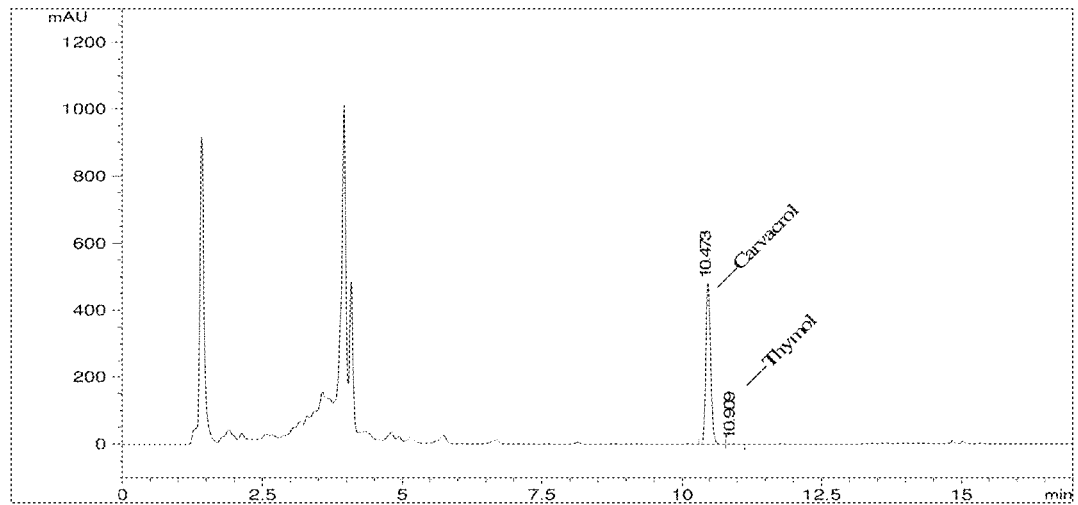
FIG. 7 – GREEK OREGANO
PRIOR ART
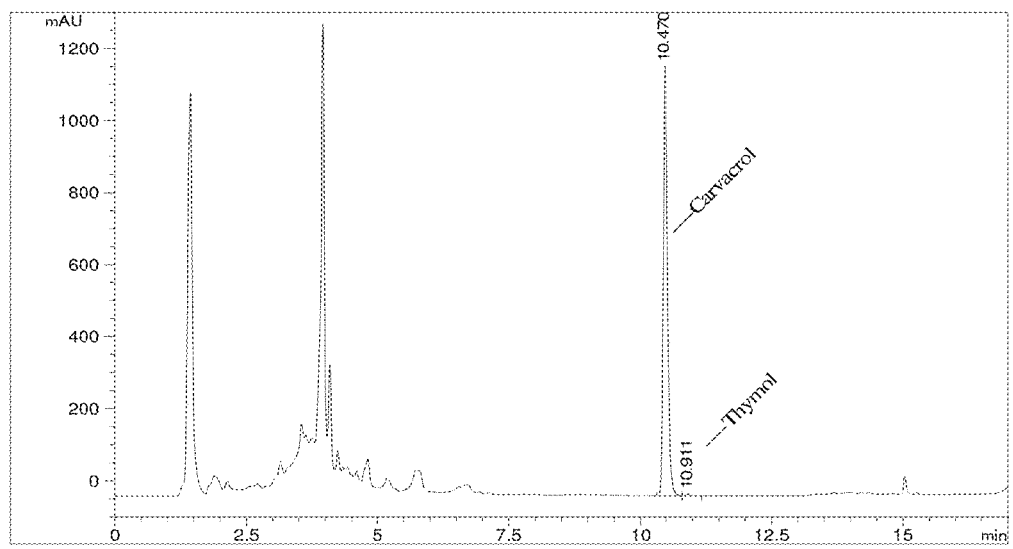
FIG. 8 – KI-1750

OREGANO CLONAL LINE HAVING HIGH LEVELS OF CARVACROL

CROSS-REFERENCE TO RELATED APPLICATIONS

This application claims priority to U.S. Provisional Patent Application Ser. No. 61/855,067, titled "Oregano Clonal Line Having High Levels of Carvacrol" which was filed on May 7, 2013, and is incorporated herein in its entirety by this reference.

FIELD OF THE INVENTION

The present invention relates generally to an oregano plant and, more specifically, to a plant of oregano clonal line KI-Ov1750 that produces a high amount of carvacrol.

BACKGROUND OF THE INVENTION

Oregano (*Orignaum* sp.) has been used for centuries as a traditional herb, spice and also in traditional medicine. Oregano essential oils are used as ingredients in several applications including tooth paste, mouth wash, gums etc. The main active molecules in oregano essential oil are carvacrol and thymol. These molecules have been shown to have potent antimicrobial activity[1] and have been used as feed additives to improve gastrointestinal health in farm animals. Oregano essential oils in animal feed diets have been shown to improve growth and reproductive performance in pigs[2,3] and overall performance in broilers. Oregano oil is also used in several personal care applications.

Accumulation of essential oil in oregano and other herbs varies with the developmental stage of the plant[4]. The highest carvacrol and thymol content in *Orignaum onites* was found at the pre-flowering stages[5]. However another study reported highest carvacrol and thymol content during the post flowering and seed formation stages in mid-June[6].

The bio active molecules, although controlled genetically, are strongly affected by environmental influences of a particular growing region; and also by agronomic conditions, harvesting time and the type of processing[4]. The age of the plants at the time of harvest seems to affect the oil yield and composition. Total thymol and carvacrol content of oregano oils obtained from younger plants was higher than that of the mature plants[4]. The amount of water received by the plant did not have a significant effect on the thymol and carvacrol content of the oil extracted from Mexican oregano[7].

The effects of temperature and duration of day light on the bioactive components of oregano essential oil have been studied. Oregano plants, like many other species, grown under higher temperatures, light intensity and longer day length periods tend to have increased oil content[8]. The harvest time was crucial to maximize the essential oil yield and the concentration of its main components in oregano. Carvacrol and thymol content were generally much higher during summer months[8].

While progressive genetic improvement was focused on increasing the essential oils, little or no effort has yet been made in the improvement of oregano for better production of carvacrol, thymol or other anti-microbial and antioxidant molecules. Extraction of carvacrol from a hyper-accumulating oregano clonal line is crucial for economically viable commercial carvacrol production. Therefore developing oregano varieties with high levels of carvacrol combined with high biomass will provide an economically valuable carvacrol source.

SUMMARY OF THE INVENTION

The invention consists of a plant of oregano named KI-Ov1750 that has elevated carvacrol levels, excellent vigor and overall agronomic robustness. The variety was selected and propagated from seeds obtained from a commercial source of segregating oregano. A plant with elevated levels of carvacrol and good growth habits was selected and has been asexually propagated to produce a clonal line of identical plants.

Plants of the clonal line KI-Ov1750 have not been observed under all possible environmental conditions. The phenotype may vary somewhat with variations in environment and culture such as temperature, light intensity, day length, water status, and/or fertilizer rate or type without, however, any variance in genotype.

An object of the present invention is a plant with a high level of carvacrol for use as an anti-microbial and antioxidant in human and animal food, beverages and personal care products.

Another object of the invention is a clonal line of oregano that is novel, stable, and uniform and has good agronomic characteristics that permit efficient cultivation of the variety as a crop that produces a high amount of biomass from which carvacrol can be extracted.

BRIEF DESCRIPTION OF THE DRAWINGS

FIG. 7 is a chromatogram of prior art Greek Oregano.

FIG. 8 is a chromatogram of the variety KI-Ov1750.

DETAILED DESCRIPTION OF THE INVENTION

Figure 1:
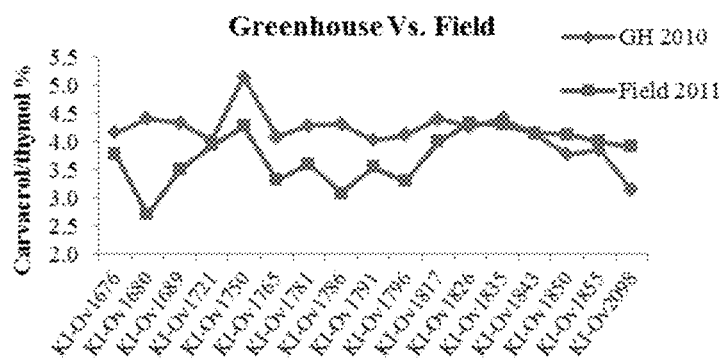
FIG. 1 is a chart comparing the carvacrol and thymol content in greenhouse-grown and filed-grown plants.

We previously identified proprietary clonal lines of oregano that can accumulate either high levels of carvacrol (Hi-C) or high levels of thymol (Hi-T) from a large scale genetic screening study under greenhouse conditions. These Hi-C and Hi-T oregano clonal lines were grown under field conditions and measured for carvacrol and thymol accumulation during the growing season as well as general biomass accumulation. The combination of target molecule accumulation, biomass production, and propagation ability has been used to identify the best clonal lines for commercial applications.

The plants of the present invention are derived from a cross between *O. vulgare* ssp. *vinculum* and *O. vulgare* ssp. *hirtum* and have the taxonomic description of being genus *Origanum*, species *vulgare*, family Lamiaceae and the common name oregano. Table 2 sets out a description of traits of the plants taken from plants growing in a greenhouse and Table 1 sets out the definitions of the traits of Table 2.

TABLE 1

Description of the traits

| | |
|---|---|
| Days to first flowering | Number of days from transplanting to when the first spike/inflorescence emerges |
| Plant height (cm) | Length of the middle stem at the time of flowering |
| Length of lateral branches (cm) | Length/Ht of the lateral stems |
| Number of lateral branches | Count on the number of lateral branches |
| Number of nodes on the middle stem | Count on the number of nodes of the middle stem |
| Internode length on the middle stem | Measure the length between 9th and 10th internode of the middle stem |
| Number leaves on the middle stem | Count the number of spikes per plant |
| Leaf width | Taken from the fully opened leaf from 10th node of the middle stem |
| Leaf length | Taken from the fully opened leaf from 10th node of the middle stem |
| Leaf area (cm$^2$) | |
| Weight of aerial part of single plant (g) | Fresh weight during of the biomass including stems |
| Leaf to stem ratio | Leaves separated from stem and weighed to obtain ratio |
| Carvacrol content | Top 6 inches of the plant cut and air dried for 48 hours for carvacrol quantitation |
| Ratio of aerial plant parts to roots | On fresh weight basis |

TABLE 2

Characteristics of KI-Ov1750 observed in the Greenhouse

| | Average | Range |
|---|---|---|
| Plant height (cm) | 76.3 cm | 61-85 cm |
| Length of lateral branches (cm) | 62.8 cm | 57-71 cm |
| Number of lateral branches | 24-38 | 30.2 |
| Number of nodes on the middle stem | 21 | 19-27 |
| Internode length on the middle stem | 2.4 cm | 2.0-3.0 cm |
| Number of leaves on the middle stem | 548-915 | 701 |
| Leaf width | 2.02 cm | 1.7-2.2 cm |
| Leaf length | 2.7 cm | 2.5-3.0 cm |
| Leaf area (cm$^2$) | 5.47 cm$^2$ | 4.25-6.6 cm$^2$ |
| Weight of aerial part of single plant (g) | 320 g | 247-366 g |
| Leaf to stem ratio | 2.48 | 2.37-2.59 |
| Carvacrol content (mg/g) during maturity | 59.92 | 57.6-69.7 |
| Ratio of aerial plant parts to roots | 1.187 | 1.01-1.45 |

In an embodiment, the plant KI-Ov1750 produces carvacrol at a level >5% on a dry matter basis during the active growing and harvest season (May to September). The present invention is related to the development of a novel, stable, uniform vigorously growing robust plant KI-Ov1750 of oregano. This plant is unique and clearly distinct from all other existing varieties of oregano. The *Origanum vulgare* plant denominated KI-Ov1750 as produced by a spearmint seed line deposited with the ATCC on Feb. 14, 2017, and assigned accession number PTA-123886.

Example 1

Selection and Development of Clonal Line

Materials and Methods

Proprietary Oregano Clonal Lines.

Seventeen oregano selections identified from the previous genetic screening were chosen to be planted under field conditions at a field site located close to Indianola, Iowa. The carvacrol content of the 14 high-carvacrol (Hi-C) oregano clonal lines and the thymol content of the three high-thymol (Hi-T) clonal lines grown under greenhouse conditions are given in Table 3.

TABLE 3

Carvacrol and thymol content of the selected oregano clonal lines grown in the greenhouse during 2010

| Clonal line* | Carvacrol % | Thymol % |
|---|---|---|
| KI-Ov1750 | 5.140 | 0.006 |
| KI-Ov1817 | 4.401 | 0.039 |
| KI-Ov1835 | 4.408 | — |
| KI-Ov1680 | 4.412 | 0.010 |
| KI-Ov1689 | 4.326 | 0.041 |
| KI-Ov1786 | 4.309 | 0.025 |
| KI-Ov1781 | 4.282 | 0.006 |
| KI-Ov1826 | 4.258 | 0.007 |
| KI-Ov1843 | 4.137 | — |
| KI-Ov1676 | 4.156 | 0.038 |
| KI-Ov1796 | 4.115 | — |
| KI-Ov1765 | 4.081 | 0.020 |
| KI-Ov1721 | 4.013 | — |
| KI-Ov1791 | 4.019 | 0.004 |
| KI-Ov1855 | 0.385 | 3.852 |
| KI-Ov1850 | 0.281 | 3.767 |
| KI-Ov2098 | 0.063 | 3.135 |

— means undetectable levels

Establishment of Field Plots.

Selected oregano clonal lines were asexually propagated as rooted cuttings at a propagation greenhouse in Texas for transplanting in late May, 2011. Approximately 38,000 plants, representing 17 selections were transplanted into field plots totaling 3.1 acres during May-June 2011, near Indianola, Iowa. Multiple strategies of weed control were employed including, mechanical tillage, hand wicking with glyphosate, hand hoeing, broadcast of selective grass herbicide (Poast), and finally broadcast spraying of a tank mix for grasses, sedges, broadleaves and weed seed germination (Poast/Basagran/Sinbar).

Tissue Sampling.

Leaf tissue was collected from each of the selections once during September, 2011 after full establishment, for carvacrol and thymol analysis. During the growing period in 2012, leaf tissue from each of the clonal lines was collected once every two weeks from April to September 2012. The top 4"-6" of leaf tissue including stems was collected from each clonal line; air dried for 48 hours and sent for analysis. A rapid method developed and validated for the determination of carvacrol and thymol in oregano dried leaf tissue was used to quantitate carvacrol and thymol content in these lines. Three replicate extractions were carried out from each bulk leaf tissue sample representing each clonal line. Carvacrol and thymol contents were determined on a per unit dry weight basis and means were calculated for statistical comparison.

Phenotype Vigor Scores.

All the clonal lines were scored for their overall vigor and growth on the basis of a visual assessment ranging from 1-5. A score of 1 was given for oregano lines with very poor vigor and growth; while a score of 5 was given to oregano lines with the best vigor and growth.

Data Analysis.

Statistical analysis was performed on the data obtained from the 17 clonal lines, using Stat Centurion Graphics in order to determine differences among clonal lines for carvacrol and thymol accumulation. Carvacrol and thymol content were analyzed using a general linear model. Fisher's least significant difference (LSD) was used to discriminate the means and was computed using multiple range tests.

Results

Variation for Carvacrol and Thymol.

There was a significant variation among clonal lines for both carvacrol and thymol content (Table 4). There was also a significant variation in sampling time for carvacrol and thymol content for each clonal line. A significant genotype (clonal line) x date of sampling was also observed (Table 4).

TABLE 4

Analysis of variance (ANOVA) for carvacrol and thymol content among genotypes sampled at different dates

| Source | Carvacrol | | | Thymol | | |
|---|---|---|---|---|---|---|
| | Df | F-Ratio | P-Value | Df | F-Ratio | P-Value |
| Clonal lines | 13 | 1077.33 | 0.0000 | 2 | 54.62 | 0.0028 |
| Replicate | 2 | 0.93 | 0.3941 | 2 | 0.12 | 0.8874 |
| Date of sampling | 10 | 5248.78 | 0.0000 | 10 | 248.42 | 0.0000 |
| Clonal lines*Date of sampling | 130 | 162.16 | 0.0000 | 20 | 76.83 | 0.0004 |

Carvacrol and Thymol Content During Year 1.

The field plots of the clonal lines were transplanted during May, 2011 and were established by August, 2011. Leaf tissue samples collected from the $1^{st}$ year growth showed reasonable carvacrol/thymol content despite experiencing transplanting stress, heavy rain and waterlogged soils (FIG. 1).

Carvacrol and Thymol Content During Year 2.

The carvacrol and thymol content of clonal lines were monitored throughout the growing season in Year 2. Carvacrol and thymol content from the leaf tissue collected semi-monthly from April to September is shown in Table 5. The carvacrol and thymol content of the clonal lines varied with growing stages throughout the growing season. During the spring regrowth period in April, the carvacrol and thymol content, irrespective of the clonal line, was at the lowest level. A gradual increase in carvacrol or thymol content was observed in all the clonal lines starting from April onwards and reached maximum levels in June.

Across clonal lines and sampling time, the highest carvacrol content was around 7% in clonal line KI-Ov1750. This clonal line consistently accumulated the highest levels of carvacrol from May to September; followed by KI-Ov1791, KI-Ov1843, KI-Ov1721, and KI-Ov1835. Amongst the three Hi-T lines planted, clonal line KI-Ov1855 did not survive the winter very well; and clonal line KI-Ov1850 showed the highest levels of thymol accumulation at >5% on a dry matter basis.

All lines were harvested twice in 2012; the first harvest during the first week of June and second harvest during the first week of September. Five Hi-C lines KI-Ov1750, KI-Ov1721, KI-Ov1791, KI-Ov1843, and KI-Ov1835 showed the highest carvacrol content with KI-Ov1750, being the highest at the time of harvest. Again during the $2^{nd}$ harvest in September, a similar trend was observed. At the time of the $2^{nd}$ harvest, KI-Ov1750 had significantly higher levels of carvacrol than other Hi-C clonal lines. On the other hand, maximum accumulation of thymol was observed only in June in clonal line KI-Ov1850 (5.16%) and the content had declined by 50% at the time of second harvest in September.

TABLE 5

Carvacrol % and thymol % from clonal lines collected from April to September[§]

| Sample | April 9$^{th}$ | April 27$^{th}$ | May 8$^{th}$ | May 22$^{nd}$ | June 4$^{th}$ | July 5th | July 20$^{th}$ | August 3$^{rd}$ | August 17$^{th}$ | August 31$^{th}$ | Sept 7$^{th}$ |
|---|---|---|---|---|---|---|---|---|---|---|---|
| 1750 | 3.03$^c$ | 3.78$^c$ | 5.76 | 6.35 | 6.97$^a$ | 6.17$^a$ | 5.09$^e$ | 5.16$^c$ | 6.21$^a$ | 6.62$^a$ | 5.54$^a$ |
| 1817 | 2.71$^d$ | 2.98$^h$ | 4.35 | 6.15 | 6.94$^a$ | 4.66$^e$ | 6.27$^a$ | 4.00$^1$ | 4.99$^f$ | 4.40$^{fg}$ | 3.18$^h$ |
| 1826 | 3.19$^b$ | 4.12$^b$ | 5.85 | 6.47 | 6.32$^b$ | 5.39$^b$ | 4.45 | 4.42$^g$ | 5.55$^d$ | 4.24$^g$ | 3.04$^i$ |
| 1835 | 3.90$^a$ | 4.89$^d$ | 5.92 | 6.91 | 6.30$^b$ | 4.72$^e$ | 4.71$^f$ | 4.50$^{fg}$ | 6.02$^b$ | 5.58$^c$ | 4.59$^c$ |
| 1689 | 2.40$^f$ | 3.63$^{de}$ | 3.57 | 5.16 | 6.24$^{bc}$ | 4.31$^f$ | 4.36$^g$ | 4.64$^f$ | 4.87$^{fg}$ | 4.46$^f$ | 3.08$^{hi}$ |
| 1791 | 3.17$^b$ | 4.21$^b$ | 4.93 | 6.81 | 6.22$^{bc}$ | 5.04$^{cd}$ | 5.72$^c$ | 5.16$^c$ | 4.71$^g$ | 4.19$^g$ | 2.77$^j$ |
| 1796 | 2.99$^c$ | 3.79$^c$ | 5.94 | 6.46 | 6.13$^c$ | 5.04$^{cd}$ | 5.05$^e$ | 3.57$^j$ | 5.23$^e$ | 4.96$^e$ | 2.76$^j$ |
| 1765 | 2.70$^d$ | 3.43$^f$ | 5.00 | 6.20 | 5.95$^d$ | 4.06$^g$ | 4.67$^f$ | 4.85$^{de}$ | 5.01$^f$ | 4.28$^g$ | 4.22$^e$ |
| 1721 | 3.15$^b$ | 4.09$^b$ | 4.82 | 5.73 | 5.93$^d$ | 5.19$^c$ | 5.09$^e$ | 5.22$^b$ | 5.48$^d$ | 5.02$^e$ | 2.75$^j$ |
| 1843 | 3.87$^a$ | 3.58$^e$ | 4.54 | 5.80 | 5.78$^{de}$ | 4.03$^h$ | 5.31$^d$ | 5.06$^{bc}$ | 5.27$^e$ | 5.53$^c$ | 4.47$^{cd}$ |
| 1676 | 2.75$^d$ | 3.30$^{fg}$ | 4.43 | 5.77 | 5.42$^e$ | 4.05$^h$ | 4.50$^g$ | 4.69$^f$ | 5.17$^e$ | 5.30$^d$ | 4.41$^d$ |
| 1786 | 2.42$^f$ | 3.74$^{cd}$ | 3.79 | 5.86 | 5.18$^f$ | 3.94$^h$ | 3.87$^h$ | 4.21$^h$ | 4.78$^g$ | 4.20$^g$ | 3.77$^g$ |
| 1781 | 2.55$^e$ | 3.26$^g$ | 4.06 | 4.98 | 5.01$^f$ | 5.16$^c$ | 5.99$^b$ | 5.86$^a$ | 5.89$^c$ | 5.74$^b$ | 4.76$^b$ |
| 1680 | 2.04$^g$ | 2.59$^i$ | 2.86 | 3.98 | 4.17$^g$ | 3.47$^i$ | 3.98$^h$ | 4.93$^d$ | 4.26$^h$ | 4.22$^g$ | 3.93$^f$ |
| LSD | 0.10 | 0.14 | 0.186 | 0.178 | 0.205 | 0.175 | 0.165 | 0.146 | 0.162 | 0.164 | 0.154 |
| 1850$^£$ | 1.86 | 2.35 | 4.16 | 4.51 | 5.16 | 4.09 | 2.69 | 2.36 | 2.87 | 2.77 | 2.53 |
| 2098$^£$ | 1.63 | 1.83 | 2.25 | 3.32 | 3.23 | 2.43 | 2.45 | 2.17 | 2.95 | 3.15 | 2.47 |

[£]KI-Ov1850 and KI-Ov2098 represents Hi-T lines

[§]Means bearing different superscripts are significantly different (p < 0.05).

Figure 2:
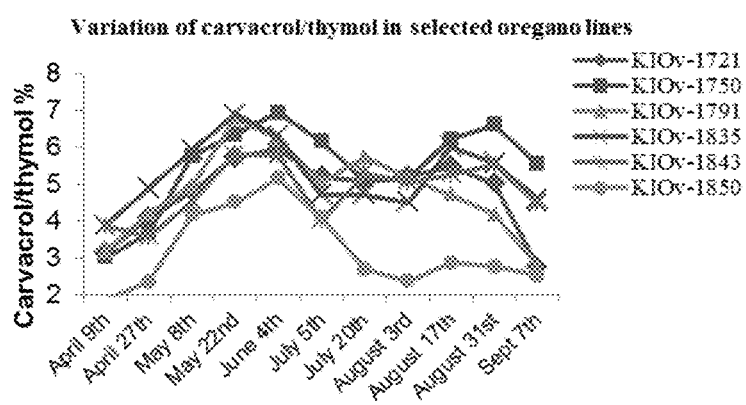
FIG. 2 is a chart of the seasonal variation of the carvacrol/thymol content in selected oregano lines.

The gradual increase in carvacrol content in the five Hi-C clonal lines (1750, 1721, 1791, 1835 and 1843); and thymol content in clonal line KI-Ov1850 is shown in the FIG. 2, below. All the Hi-C clonal lines showed the highest level of carvacrol content during the first week of June and again during the last week of August. The Hi-T clonal line KI-Ov1850, showed the highest thymol content in June with no second peak later in the summer.

HPLC was performed on prior art Greek Oregano (FIG. 8) and the present invention (FIG. 9), demonstrating the low thymol and high carvacrol content of the present subject line.

Phenotype Vigor Scores.

Figure 3:
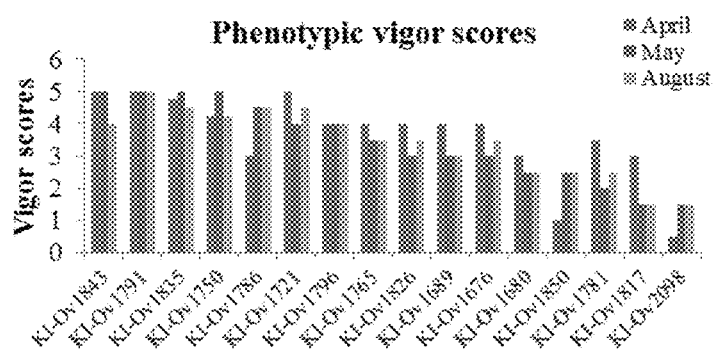
FIG. 3 is a chart of the relative phenotypic vigor scores of selected oregano lines.
Figure 4:
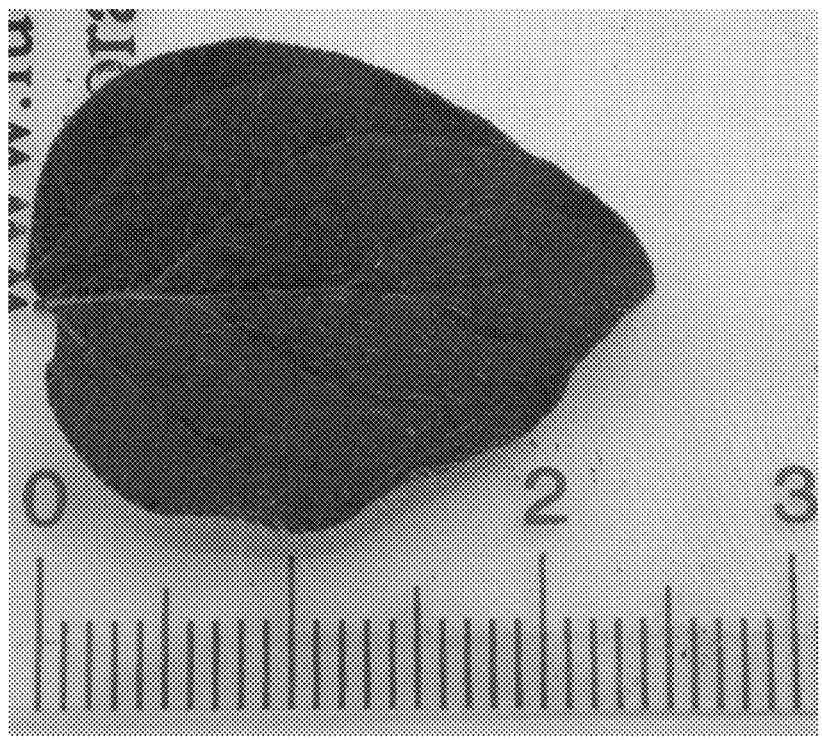
FIG. 4 is a photograph of the length of a leaf of a plant of the variety KI-Ov1750 against a centimeter scale.
Figure 5:
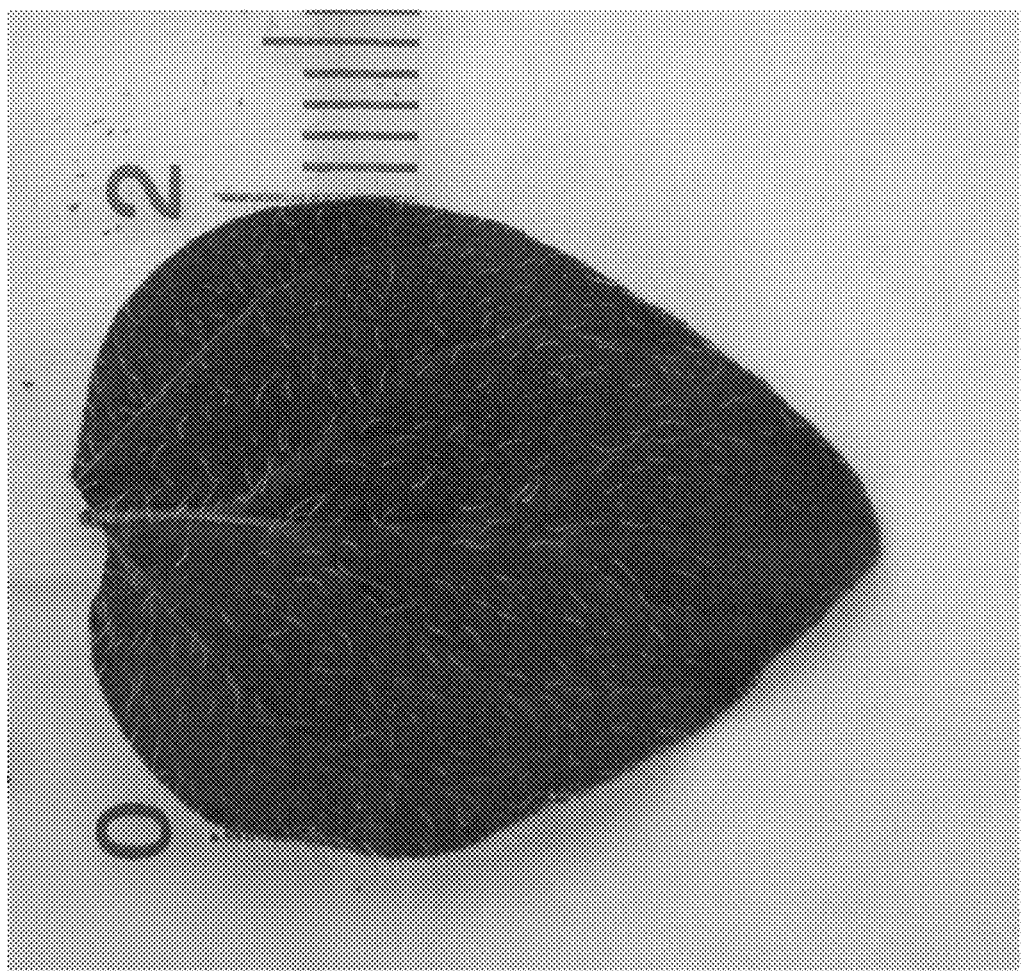
FIG. 5 is a photograph of the width of a leaf of a plant of the variety KI-Ov1750 against a centimeter scale.
Figure 6:
FIG. 6 is a photograph of a lateral branch of the variety KI-Ov1750.

All the clonal lines were scored for the overall plant vigor and growth during the growing period. Clonal lines (1843, 1791, 1835 and 1750) consistently exhibited vigorous growth throughout the growing period (FIG. 3). Of all the lines, KI-Ov1843 flowered much earlier than the other lines.

Discussion

Previously, we had identified several proprietary Hi-C (14 clonal lines with carvacrol content >4%) and Hi-T (3 clonal lines with thymol content >3%) oregano clonal lines under the greenhouse conditions. These lines were grown in Iowa to monitor the accumulation of carvacrol and thymol under field conditions during 2011. Understanding the fluctuations of carvacrol and thymol content during the growing season is essential in order to harvest biomass in time to maximize the yield of carvacrol and thymol. The first year was mainly focused on establishing these clonal lines in the field. The carvacrol and thymol accumulation was not at the maximum during the first year of growth.

During the $2^{nd}$ year of growth in 2012, carvacrol and thymol content was monitored in these lines throughout the growing season from April to September. Clonal line KI-Ov1750 consistently accumulated the highest levels of carvacrol throughout the growing season. Other clonal lines (KI-Ov1791, KI-Ov1843, KI-Ov1721, and KI-Ov1835) also showed higher levels of carvacrol (>5%) relative to the rest of the clonal lines tested. Amongst the three Hi-T lines planted, KI-Ov1855 did not survive the winter, while KI-Ov1850 showed the highest levels of thymol accumulation in Year 2. The data from Year 1 was not correlated to Year 2 since Year 1 was mostly considered as the establishment year. Clonal line KI-Ov1750 had the highest content of carvacrol at up to 7% on a dry matter basis at the time of harvest in June; and 6.7% at the time of harvest in September. Clonal line KI-Ov1850 had the highest content of thymol at up to 5.2% on a dry matter basis at the time of harvest in June. The lack of a second peak accumulation later in the summer may have been a function of the very hot and dry conditions experienced during 2012. In general, the most common oregano grown commercially is Greek oregano (*Origanum vulgare*, sub species *hirtum*). Greek oregano has also been reported to have unusually high levels of carvacrol and thymol. Assessment of carvacrol and thymol content in Greek oregano and common oregano (cv. Hot & Spicy) was shown by us to be <3% on a dry matter basis. Carvacrol and thymol hyper-accumulation >5% on a dry matter basis has not previously been reported to our knowledge. This makes clonal lines 1750, 1721, 1791, 1843 and 1850 unique and patentable as commercially viable sources of carvacrol and thymol, respectively. Clonal lines (#1843, 1791, 1835 and 1750) consistently exhibited vigorous growth throughout the growing period despite the fact that these plots underwent water stress due to lack of rain during the summer of 2012. KI-Ov1843 flowered much earlier than the other lines during Year 2.

The essential oil and their contents were reported to be at the highest during the pre-flowering stage[5]. All the clonal lines were flowering at the time of harvest during the first week of June and yet the carvacrol and thymol content were found to be at the maximum levels. Hence oregano can be harvested either pre-flowering or at flowering in order to maximize the carvacrol and thymol yield. Under suitable growing conditions, with adequate rainfall, these lines could be harvested twice during the growing season; once during late May and again during the last week of August. Hi-C clonal lines KI-Ov1750 and KI-Ov1721; and Hi-T clonal line, KI-Ov1850 will be advanced to large scale commercial field planting.

Evidence of Uniformity and Stability

No variants of any kind have been observed since the variety KI-Ov1750 was identified, indicating the stability and uniformity of the genotype. It is clear from these results that the KI-Ov1750 clonal line is stable and reproduces true to type in successive generations of asexual reproduction.

Statement of Distinction

KI-Ov1750 is more vigorous and generates more biomass per acre than any other Hi-C line tested in our program and consistently produces higher per dry weight of carvacrol than either Greek or Mexican oregano. Due to vigorous vegetative growth this genotype can be harvested multiple times in a season and has the potential of growing in any temperate climate.

DNA sample from KI-Ov1750 extracted from tissue was sequenced by Data2Bio, LLC (Ames, Iowa) in two Ilumina HiSeq 2000 paired-end (PE) lanes (lanes 5 and 6). Each genomic DNA sample was prepared using the Illumina protocol outlined in "TruSeq DNA Sample Preparation Guide" (Catalog#PE-940-2001). First, gDNA was fragmented (Covaris Sherainy duration time 120 sec) to produce 300-400 bp inserts. The DNA fragment ends were repaired and phosphorylated using Klenow, T4 DNA polymerase and T4 polynucleotide kinase. Next, an "A" base was added to the 3' end of the blunted fragments, followed by ligation of lumina adapters via T-A mediated ligation. The ligated products were size selected by AMPure XP Beads and then PCR amplified using Illumina primers. The library size and concentration were determined using an Agilent Bioanalyzer 1000 chip. Raw reads from both lanes were combined into a single archive and summarized in Table 6.

TABLE 6

Summary of Raw Sequence Reads

| | RAW READS | | |
|---|---|---|---|
| File Name | No. Reads | Base Pairs | Read Length (BP) |
| KI-1750-1-1_1 | 476,210,409 | 48,097,251,309 | 101 |
| KI-1750-1-1_2 | 476,210,409 | 48,097,251,309 | 101 |
| KI-1750 total | 952,420,818 | 96,194,502,618 | 101 |

The nucleotides of each raw read were scanned for low quality. Bases with PHRED quality value <15 (out of 40) (Ewing, B. and P. Green, 1998 Base-calling of automated sequencer traces using phred. II. Error probabilities. *Genome Res.* 8(3): 186-194), i.e., error rates of ≤0.03%, were removed by the trimming pipeline. Each read was examined in two phases. In the first phase reads were scanned starting at each end and nucleotides with quality values lower than the threshold were removed. The remaining nucleotides were then scanned using overlapping windows of 10 bp and sequences beyond the last window with average quality value less than the specified threshold were truncated. The trimming parameters were referred to the trimming software, Lucy (Chou, H. H., G. Sutton, A. Glodek and J. Scott, 1998 Lucy—A Sequence Cleanup Program, pp. in *Proceedings of the Tenth Annual Genome Sequencing and Annotation Conference (GSAC X)*, Miami, Fla.). A statistical summary of raw reads is shown in Table 7.

TABLE 7

Summary of Raw Reads Trimming

| | RAW READS | | |
|---|---|---|---|
| File Name | No. Reads | Base Pairs | Read Length (BP) |
| KI-1750-1-1_1 | 476,210,409 | 48,097,251,309 | 101 |
| KI-1750-1-1_2 | 476,210,409 | 48,097,251,309 | 101 |
| KI-1750 total | 952,420,818 | 96,194,502,618 | 101 |

| | TRIMMED READS | | |
|---|---|---|---|
| File Name | No. Reads (%, trimmed/raw) | Base Pairs (%, trimmed/raw) | Read Length (BP) |
| KI-1750-1-1_1 | 474,550,357 (99.7%) | 46,594,179,642 (96.9%) | 99 |
| KI-1750-1-1_2 | 463,557,402 (97.3%) | 44,994,775,061 (93.5%) | 98 |
| KI-1750 total | 938,107,759 (98.5%) | 91,588,954,703 (95.2%) | 98 |

The raw sequences have been deposited and uploaded to the Sequence Read Archive (SRA) database of the National Center for Biotechnology Information (NCBI), U.S. National Library of Medicine, Bethesda, Md., and those sequences are incorporated herein in their entirety by this reference. The submission accession assigned by NCBI is SRX220839 and it was released to the public on May 7, 2013. Those skilled in the art can analyze the deposited raw sequence information to determine the genetic sequence of KI-Ov1750.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

REFERENCES

1. Bendahou M, Muselli A, Grignon-Dubois M, Benyoucef M, Desjobert J M, Bernardini A F, Costa J 2008 Antimicrobial activity and chemical composition of *Origanum glandulosum* Desf. essential oil and extract obtained by microwave extraction: Comparison with hydrodistillation. Food Chemistry. 106:132-139. SA-10-02422
2. Manzanilla E G, Perez J F, Martin M, Kamel C, Baucells F and Casa J 2004 Effect of plant extracts and formic acid on the intestinal equilibrium of early-weaned pigs. Journal of Animal Science 82, 3210-3218. SA-08-03666
3. Allan P and G. Bilkei. 2005 Oregano improves reproductive performance of sows. Theriogenology 63, 716-721. SA-10-00360
4. Sangwan, N. S, Farooqi, A. H. A, Shabih F, and Sangwan R. S. 2001 Regulation of essential oil production in plants. Plant Growth Regulation. 34. 3-21 SA-12-02838
5. Toncer O, Karaman S, Kizil S and Diraz E. 2009 Changes in essential oil composition of oregano (*O. onites* L.) due to diurnal variations at different developmental stages. Notulae Botanicae Hord Agrobotanici 37:177-181 SA-12-02837
6. Yaldiz G, Sekeroglu N, Ozguven M and Kirpik M 2005. Seasonal and diurnal variability of essential oil and its components in *Origanum onites* L. grown in the ecological conditions of Cukurova. Grasas. Y. Aceites. 56: 254-258 SA-12-02839
7. Dunford N T and Vazquez R. S. 2005 Effect of water stress on plant growth and thymol and carvacrol concentrations in Mexican oregano grown under controlled conditions. Journal of Applied Horticulture. 7:20-22. SA-12-02863
8. Putievsky E, Dudai N, and Ravid U. 2005 Cultivation, selection and conservation of Oregano species in Israel conditions. Proceedings of the IPGRI International Workshop on Oregano 8-12 May 1996, CIHEAM, Valenzano, Bari, Italy SA-12-02864

We claim:

1. A method of extracting carvacrol, comprising extracting carvacrol from plant tissue of an oregano *Origanum vulgare* plant denominated KI-Ov1750 which has been deposited with the ATCC and assigned accession number PTA-123886.

2. The method of claim 1, wherein the plant tissue is selected from the group consisting of leaf, pollen, root, seed, or stem tissue.

3. The method of claim 1, further comprising adding the carvacrol to a composition, wherein the carvacrol acts as an antimicrobial agent.

4. The method of claim 1, wherein the plant tissue comprises greater than 5% carvacrol on a dry weight basis after drying.

5. The method of claim 1, further comprising adding the carvacrol to a composition, wherein the carvacrol acts as an antioxidant.

6. The method of claim 5, further comprising adding the antioxidant to a product selected from the group consisting of: human food, animal food, beverages and personal care products.

7. The method of claim 1, further comprising adding or applying the carvacrol to animal feed in order to improve gastrointestinal health in farm animals.

8. A method of providing an antimicrobial agent, comprising extracting carvacrol from plant tissue of an oregano *Origanum vulgare* plant denominated KI-Ov1750 which has been deposited with the ATCC and assigned accession number PTA-123886 and adding the carvacrol to a composition, wherein the carvacrol is effective as an antimicrobial agent.

9. The method of claim 8, wherein the antimicrobial agent is added to a composition selected from the group consisting of: human food, animal food, beverages or personal care products.

10. The method of claim 8, further comprising adding or applying the carvacrol to animal feed in order to improve gastrointestinal health in farm animals.

11. The method of claim 8, wherein the plant tissue comprises greater than 5% carvacrol on a dry weight basis after drying.

\* \* \* \* \*